United States Patent
Nishibayashi

(10) Patent No.: US 8,671,784 B2
(45) Date of Patent: Mar. 18, 2014

(54) BODY MOVEMENT DETECTING APPARATUS AND BODY MOVEMENT DETECTING METHOD

(75) Inventor: Kenji Nishibayashi, Tokyo (JP)

(73) Assignee: Tanita Corporation, Tokyo (JP)

( * ) Notice: Subject to any disclaimer, the term of this patent is extended or adjusted under 35 U.S.C. 154(b) by 294 days.

(21) Appl. No.: 12/748,155

(22) Filed: Mar. 26, 2010

(65) Prior Publication Data

US 2010/0256532 A1    Oct. 7, 2010

(30) Foreign Application Priority Data

Apr. 2, 2009    (JP) ................ 2009-090112

(51) Int. Cl.
- *A61B 5/00* (2006.01)
- *G01L 5/16* (2006.01)
- *A61B 5/103* (2006.01)
- *A61B 5/117* (2006.01)

(52) U.S. Cl.
USPC .............................. 73/865.4; 600/595; 702/19

(58) Field of Classification Search
USPC ..................... 600/300, 595; 702/19; 73/865.4
See application file for complete search history.

(56) References Cited

U.S. PATENT DOCUMENTS

| | | | |
|---|---|---|---|
| 5,989,200 A * | 11/1999 | Yoshimura et al. | 600/587 |
| 2005/0172311 A1 | 8/2005 | Hjelt et al. | |
| 2005/0240086 A1 * | 10/2005 | Akay | 600/300 |
| 2006/0167387 A1 | 7/2006 | Buchholz et al. | |
| 2007/0051369 A1 | 3/2007 | Choi et al. | |
| 2007/0238938 A1 * | 10/2007 | Nishibayashi et al. | 600/301 |
| 2008/0262392 A1 * | 10/2008 | Ananny et al. | 600/595 |
| 2008/0275348 A1 * | 11/2008 | Catt et al. | 600/483 |
| 2009/0143199 A1 * | 6/2009 | Nishibayashi | 482/8 |

FOREIGN PATENT DOCUMENTS

| | | |
|---|---|---|
| JP | 2002-191580 | 7/2002 |
| JP | 2006-101973 | 4/2006 |
| WO | WO 01/52718 A2 | 7/2001 |

OTHER PUBLICATIONS

European Search Report issued in European Patent Application No. 10156574.5-1265, mailed Jun. 23, 2010.
Japanese Office Action issued in Japanese Patent Application No. 2009-090112, mailed Feb. 4, 2011.

* cited by examiner

*Primary Examiner* — Max Hindenburg
*Assistant Examiner* — John Pani
(74) *Attorney, Agent, or Firm* — McDermott Will & Emery LLP

(57) ABSTRACT

There is provided a body movement detecting apparatus including: a body movement data acquiring unit configured to detect a body movement of a user and acquire body movement data relating to the body movement; a memory unit configured to memorize the body movement data corresponding to the type of an activity of the user as registered body movement data; a body movement determining unit configured to compare the body movement data acquired by the body movement data acquiring unit with the registered body movement data and determine the type of the activity of the user; and a computing unit configured to be able to calculate consumed energy by the body movement corresponding to the type of the activity determined by the body movement determining unit.

18 Claims, 8 Drawing Sheets

BODY MOVEMENT DETECTING APPARATUS AND BODY MOVEMENT DETECTING METHOD

BACKGROUND OF THE INVENTION

1. Field of the Invention

The present invention relates to a body movement detecting apparatus and a body movement detecting method for detecting body movements of a user and calculating energy consumed by the body movements.

2. Description of the Related art

In the related art, there is a pedometer as one of body movement detecting apparatuses, and more specifically, those added with a calculating function of consumed energy are widely distributed. The pedometer as described above is configured to count the number of steps (step) of the user made by walking (including running, hereinafter), and to calculate consumed energy according to the number of steps. As another body movement detecting apparatus, for example, the one disclosed in JP-A-2002-191580 is proposed. The body movement detecting apparatuses including the pedometer in the related art as described above are configured to perform a process to detect or not to detect the body movements which satisfy preset conditions irrespective of the person who uses the apparatus.

However, the users of the body movement detecting apparatuses are as diverse as students, workers, homemakers and so on and have different life styles, respectively, so that the state of usage of the body movement detecting apparatus is different from user to user. When an activity such as walking is performed for example, the way of walking is different from user to user, and hence the state of usage is different from user to user even though the type of the activity is the same. Therefore, with the apparatuses which detect the body movement always under certain conditions for all users and calculate the consumed energy as the body movement detecting apparatus in the related art, the calculation of the consumed energy in which characteristics of the body movement of individual users are taken into consideration cannot be achieved.

In view of such circumstances, it is an object of the present invention to provide a body movement detecting apparatus and a body movement detecting method which are capable of calculating consumed energy by determining a type of a body movement on the basis of a reference of the individual user.

In order to solve the above-described problems, there is provided a body movement detecting apparatus including: a body movement data acquiring unit configured to detect a body movement of a user and acquire body movement data relating to the body movement; a memory unit configured to memorize the body movement data corresponding to a type of an activity of the user as registered body movement data; a body movement determining unit configured to compare the body movement data acquired by the body movement data acquiring unit with the registered body movement data and determine the type of the activity of the user; and a computing unit configured to be able to calculate consumed energy by the body movement corresponding to the type of the activity determined by the body movement determining unit.

In the body movement detecting apparatus according to the invention, the computing unit is capable of calculating the consumed energy using a body activity strength determined by the type of the activity.

The body movement detecting apparatus according to the invention includes an input unit being capable of inputting the type of the activity of the user, and the registered body movement data is body movement data acquired by the body movement data acquiring unit and memorized in the memory unit in correspondence with the type of the activity input by the input unit.

In the body movement detecting apparatus according to the invention, the memory unit memorizes one or more types of the activities together with body activity strengths for the respective types of the activities, and the user is allowed to operate an input unit to select a desired type of the activity from the types of the activities memorized in the memory unit, and causes the registered body movement data to be memorized in the memory unit.

In the body movement detecting apparatus according to the invention, the memory unit memorizes the types of the activities except for walking and/or running together with the body activity strengths for the respective types of the activities, the body movement determining unit is capable of determining whether or not the user is walking and/or running by a predetermined threshold value relating to the body movement data acquired by the body movement data acquiring unit, and the computing unit calculates the consumed energy on the basis of a body activity strength calculated on the basis of a body movement strength of the body movement data when the body movement determining unit determines that the user is walking and/or running, and on the basis of the body activity strength determined by the type of the activity of the registered body movement data when the body movement determining unit determines that the user is not walking and/or running.

In the body movement detecting apparatus according to the invention, the computing unit calculates the consumed energy on the basis of the body activity strength determined by the type of the activity of the registered body movement data when the body movement determining unit determines that there are the registered body movement data corresponding to the body movement data acquired by the body movement data acquiring unit, and calculates the consumed energy on the basis of the body activity strength calculated on the basis of a body movement strength of the body movement data when the body movement determining unit determines that there is no registered body movement data corresponding to the body movement data.

There is provided a body movement detecting method includes: a body movement acquiring step configured to detect a body movement of a user and acquire body movement data relating to the body movement; a registered body movement data acquiring step for memorizing the body movement data corresponding to a type of an activity of the user as registered body movement data; a body movement determining step for comparing the body movement data acquired by a body movement data acquiring unit after the registered body movement data acquiring step with the registered body movement data and determining the type of the activity of the user; and an energy computing step being able to calculate consumed energy by the body movement corresponding to the type of the activity determined by a body movement determining unit.

ADVANTAGES OF THE INVENTION

The body movement detecting apparatus and the body movement detecting method which are capable of calculating the consumed energy by determining the type of the body movement on the basis of the reference of the individual user are provided.

DESCRIPTION OF PREFERRED EMBODIMENT

Figure 1:
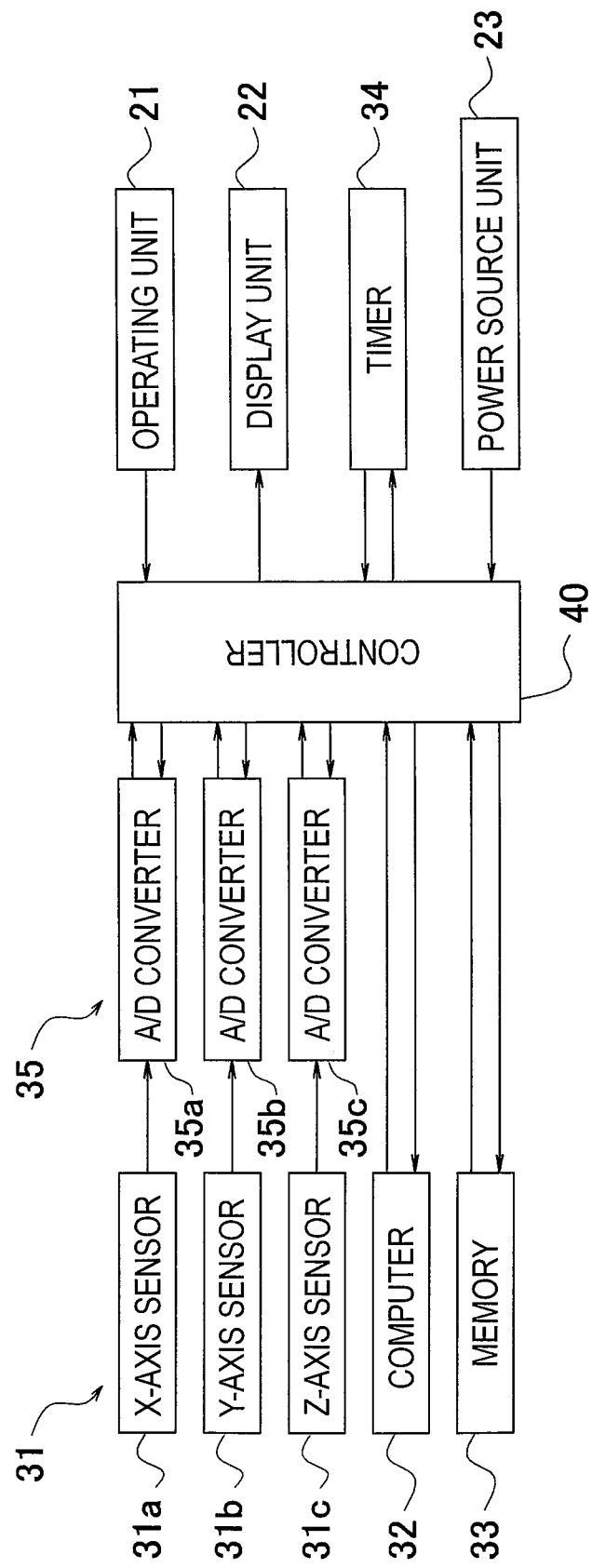
FIG. 1 is a block diagram showing a configuration of a body movement detecting apparatus according to the invention.

Referring now to the drawings, a body movement detecting apparatus according to an embodiment of the invention will be described. FIG. 1 is a block diagram showing a configuration of a body movement detecting apparatus 10. As shown in FIG. 1, the body movement detecting apparatus 10 includes an operating unit 21, a display unit 22, a power source unit 23, an accelerator sensor 31, a computer 32, a memory 33, a timer 34, an A/D converter 35, and a controller 40. Detailed configurations of the respective members will be described below.

In the invention, the term "body movement data" means data on the body movements of a user. More specifically, they are data reflecting the body movements of the user (for example, walking, running, and activities other than those (daily life actions)) such as body movement data relating to the stress of the body movement (body movement strength), repetitiveness and continuity of the body movement, pitches of the body movement when the same body movement is repeated (body movement pitch), the number of times (for example, the number of steps), and includes registered body movement data described later. As the body movement strength, using data relating to acceleration values of the body movement of the user is specifically preferable. The data relating to the acceleration value may be selected as needed from, for example, a value obtained by subtracting a lower peak value from an upper peak value for each body movement, acceleration values themselves for each body movement, or an integrated value of the acceleration values ("magnitudes of the acceleration values") per a given period. The body movement includes general actions (activities) of the body of the user, and includes walking, running, and, in addition, other activities (for example, a step action without or little repetitiveness or continuity, an action only of the upper half body, mainly, daily life actions).

The term "registered body movement data" means body movement data corresponding to the types of the activity of the individual user of the body movement detecting apparatus 10, and is one or more body movement data which are to be registered in the body movement detecting apparatus 10 in advance. In this embodiment, for example, a plurality of the types of the activities of the registered body movement data, which can be registered, such as first registered body movement data "walking", second registered body movement data "running", third registered body movement data "watching TV or listening to music in a quietly sitting position" (resting state), fourth registered body movement data "light work in an office", fifth registered body movement data "housework 1 (laundry)", sixth registered body movement data "housework 2 (cleaning)", seventh registered body movement data "housework 3 (washing dishes) are listed up so as to allow the user to select and register desired items (see FIG. 3 and FIG. 4).

The term "body activity strength" means an index which is represented by how many times the strength of the body activity of a person corresponds to with respect to the strength of the body activity of the person in the resting state. For example, it is determined for various body activities of the person in advance, such as "3" for the normal walking, "7" for running with reference to "1" for a state of being at rest in a sitting position. This corresponds to "METs (Metabolic Equivalents)" in "Exercise Guideline for Health Body 2006" formulated in July in 2006 by an investigative commission for formulating the required amount of exercise and exercise guideline.

The term "amount of body activity strength" is an index which represents the amount of the body activity, and is obtained by the body activity strength multiplied by the duration of the body activity. This corresponds to "EXERCISE" in the "Exercise Guideline for Health Body 2006" described above.

The operating unit 21 (biological data acquiring unit, input unit) functions mainly as a data input unit for inputting the biological data of the user or inputting setting items of the body movement detecting apparatus 10, and allows the user to select or input the types of activities, described later. The number, the shape, and the operating method of the operating unit 21 are not specifically limited, and may be selected as needed from, for example, those of a push-button type, a touch sensor type, and a dial type. Here, as the biological data to be input by the operating unit 21, weight, height, age, and sex may be exemplified for example. However, the biological data are not specifically limited as long as they are needed for obtaining consumed energy by the body movement of the user. The setting items are setting items required when the user uses the body movement detecting apparatus 10, and initial settings of the body movement detecting apparatus 10, the current date and time, the day of week and time of day of the present, change-over of contents to be displayed on the display unit 22 are exemplified for example. The biological data and the setting items input in this manner are memorized in the memory 33 (for example, RAM (Random Access Memory) under control of the controller 40, and are displayed on the display unit 22.

The display unit 22 is a data display unit for displaying data transmitted from the controller 40, and mainly displays the biological data and the setting items of the user (including the types of activities described later), an operation guide, current time of day, date, day of week, accumulated consumed energy, number of steps, amount of body activities, walk distance, time length of activities other than the walking, and resting time length of the corresponding day, and data of past several days. The contents to be displayed are memorized in the memory 33, and the controller 40 is configured to read out data from the memory 33 according to the state of usage of the body movement detecting apparatus 10 according to a program memorized in the memory 33 in advance, and displays on the display unit 22. For example, a display unit employing an LCD (Liquid Crystal Display) may be used as the display unit 22, and the display unit 22 and the operating unit 21 may be formed integrally as a liquid crystal display panel having, for example, a touch panel function.

The power source unit 23 is a power supply unit made up of a power supply source such as a battery, so that power is supplied to the respective components of the body movement detecting apparatus 10 via the controller 40.

The body movement detecting apparatus 10 includes the accelerator sensor 31, the computer 32, the memory 33, the timer 34, the A/D converter 35, and the controller 40 as an internal mechanism. The computer 32 and the controller 40 each are preferably formed by an integrated circuit, and the computer 32 and the controller 40 may be integrated.

The memory 33 is a memory unit made up of a volatile memory (not shown), or a non-volatile memory (not shown). The volatile memory is configured to be able to memorize a variety of data for the processes by the controller 40 temporarily. It also functions as the memory area used by the computer 32 for a computing process. The non-volatile memory is used for storing data to be memorized for a long term. For example, memorization of the registered body movement data (including determination values) as described later, the non-volatile memory is configured to be used for storing past body movement data (including determination values) on the basis of day of week and time of day, biological data input by the user, consumed energy calculation formulas, and a variety of programs as described later.

The timer 34 measures elapse of predetermined time and determines whether or not the predetermined time is elapsed and, for example, is able to measure the elapsed time from a moment when the user starts to use the body movement detecting apparatus 10, or to determine body movement pitches of the user (for example, time required for one step). In the embodiment, the timer 34 is an independent component. However, it may be integrated into the controller 40 as a timer circuit to determine whether the predetermined time is elapsed or not by the controller 40 by itself.

The accelerator sensor 31 is a body movement data acquiring unit configured to acquire the body movement data relating to the body movement of the user, and is a sensor which outputs values varying according to the acceleration values generated by the body movement of the user. More specifically, the accelerator sensor 31 includes an X-axis sensor 31a, a Y-axis sensor 31b, and a Z-axis sensor 31c (see FIG. 1), so as to be capable of detecting the body movement in the 3-axis (X-axis, Y-axis, Z-axis) directions orthogonal to each other, and is configured to be able to acquire acceleration values, which is a value obtained by combining respective output values from the X-axis sensor 31a, the Y-axis sensor 31b, and the Z-axis sensor 31c. In the embodiment, the accelerator sensor 31 is used as the body movement data acquiring unit, and hence the body movement strength of the user corresponds to the data relating to the acceleration values. Therefore, the body movement data is obtained in such a manner that the body movement strength is determined to be strong if the acceleration value is high, and the body movement strength is determined to be weak if the acceleration value is low.

The output acquired by the accelerator sensor 31 is converted from analogue to digital by the A/D converter 35 for the processes performed by the controller 40 or the computer 32. More specifically, the respective output values as analogue data acquired by the X-axis sensor 31a, the Y-axis sensor 31b, and the Z-axis sensor 31c are converted into digital data respectively by an A/D converter 35a, an A/D converter 35b, and an A/D converter 35c, and are memorized in the memory 33 corresponding to the elapsed time from the start of acquisition in conjunction with the timer 34. Also, by combining the A/D converted values of the respective output values from the X-axis sensor 31a, the Y-axis sensor 31b, and the Z-axis sensor 31c by the computer 32, acceleration values (the A/D converted value of the acceleration values) as digital data are obtained by calculation, and are memorized in the memory 33 corresponding to the elapsed time from the start of acquisition in conjunction with the timer 34. In this manner, by acquiring the acceleration values corresponding to the elapsed time, not only the body movement strength, but also the presence or absence of the repetitiveness or continuity of the body movement, the pitch (body movement pitch) or the number of times (for example, the number of steps) when the same body movement is repeated may be acquired simultaneously as the body movement data by observing the acceleration value in time series in sequence of acquisition. In order to acquire the acceleration values by all the body movements of the user accurately by this accelerator sensor 31, the body movement detecting apparatus 10 is preferably mounted to the user so as to be in contact thereto as close as possible and, it is recommended to propose a state of being attached, for example, on a belt or the like worn by the user around the waist, or a state of being memorized in a chest pocket of a dressing of the user specifically for enabling sensing of the body movement of the upper half body as well. The body movement data acquired in this manner is memorized in the memory 33 and is partly (for example, the number of steps) displayed on the display unit 22 by the control of the controller 40.

As shown in FIG. 1, the controller 40 is electrically connected to the operating unit 21, the display unit 22, the power source unit 23, the accelerator sensor 31, the computer 32, the memory 33, the timer 34, and the A/D converter 35 so that the respective operations are controlled by the controller 40.

The controller 40 functions as a body movement determining unit configured to determine which one of the registered body movement data already registered the body movement data acquired at the instance just passed by the accelerator sensor 31 in association with the computer 32, described later. More specifically, the controller 40 compares determination values of the body movement data acquired individually per the predetermined unit time with determination values of one or more registered body movement data after the initial setting, and determines which registered body movement data they correspond to. Here, the determination values are not specifically limited as long as they are able to reflect the characteristics of the body movement data, and a detailed example will be described later.

The controller 40 further functions as a number-of-steps counting unit. An example of a number-of-steps counting method performed by the controller 40 will be described in brief below. The controller 40 causes the A/D converter 35 to convert the acceleration values acquired by the accelerator sensor 31 from analogue to digital and causes the memory 33 to memorize the acquired digital acceleration values in sequence in time series and, for example, acquires a waveform by plotting all the A/D converted values of acceleration values acquired in sequence with a lateral axis indicating the elapsed time (unit: second) and a vertical axis indicating the A/D converted value of the acceleration value (unit: count), and then performs the following process according to the transition of the acceleration value. The amplitude of the waveform of the acceleration value is determined as one step of walking (when the value exceeds a first threshold value X and is acquired within a given period t1), whether a predetermined number of such waves or larger appear within the predetermined time (whether or not the number of waves in the waveform of the acceleration value within a given period t2 exceeds a second threshold value Y) is determined. If the number of the waves is the predetermined number of waves or larger, it is determined to be a continuous walking, so that the steps are counted by incrementing by one at every peak value.

The computer 32 is a computing unit being capable of performing a variety of computing processes under control of the controller 40 and, for example, calculates consumed energy by the body movement of the user on the basis of the biological data or the body movement data of the user memorized in the memory 33. Calculation of the consumed energy is performed by cumulatively adding the consumed energy of the body movement data (body movement data acquired at the instance just passed) at every predetermined unit time (for example 20 seconds).

More specifically, the controller 40 compares the determination values of the body movement data acquired per the predetermined unit time with the determination values of the one or more registered body movement data registered in advance, determines which one of the registered body movement data relating to the type of the activity they correspond to, reads the body activity strength defined by the determined type of the activity, that is, memorized corresponding to the registered body movement data relating to the determined type of the activity, and sends it to the computer 32. What the computer 32 should do is to calculate the amount of the body activity obtained by multiplying the body activity strength by the predetermined unit time and to obtain the consumed energy on the basis of the predetermined consumed energy calculation formula using the amount of body activity and, for example, to calculate the consumed energy in the predetermined unit time, for example, by multiplying the amount of the body activity by the weight of the user which is registered in advance, and a predetermined coefficient. By cumulatively adding the consumed energy in the predetermined unit time calculated in this manner, for example, the total consumed energy of the corresponding day of usage is calculated.

A body movement detecting method using the body movement detecting apparatus 10 will be described.

Figure 2:
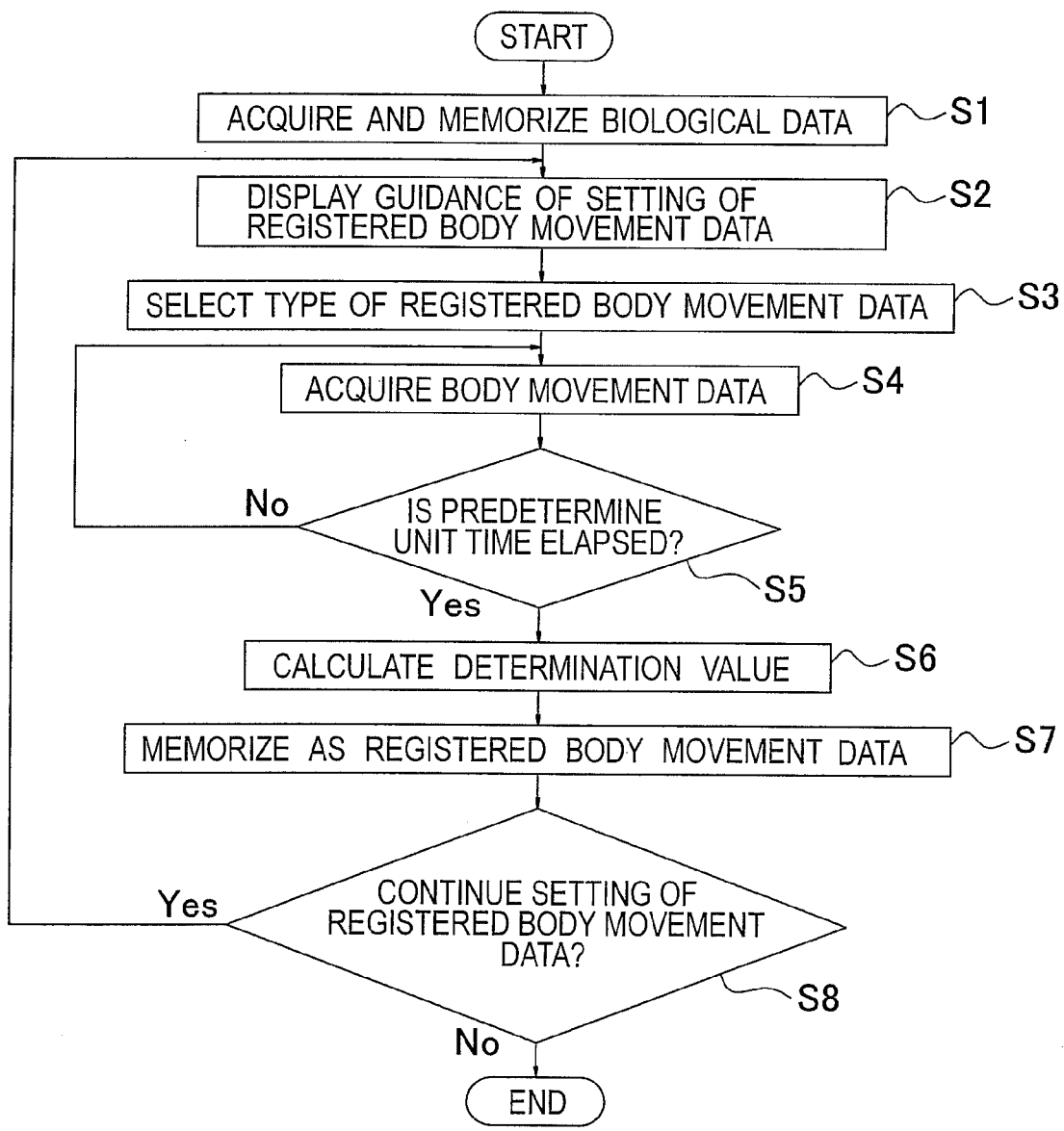
FIG. 2 is a flowchart showing an example of a flow of an initial setting of the body movement detecting apparatus according to the invention.
Figure 3A:
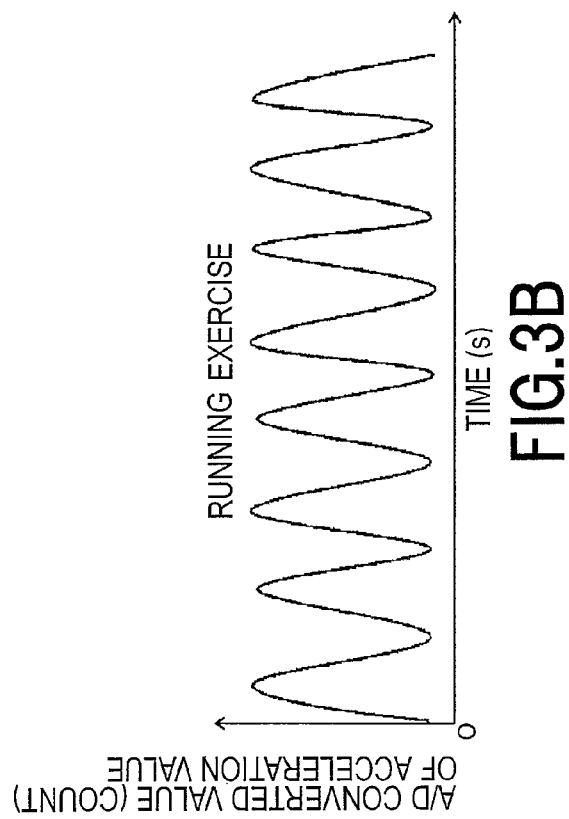
FIG. 3A is a drawing showing a waveform of an A/D converted value of an acceleration value as first registered body movement data in an example of registered body movement data to be registered in the initial setting of the body movement detecting apparatus.
Figure 3B:
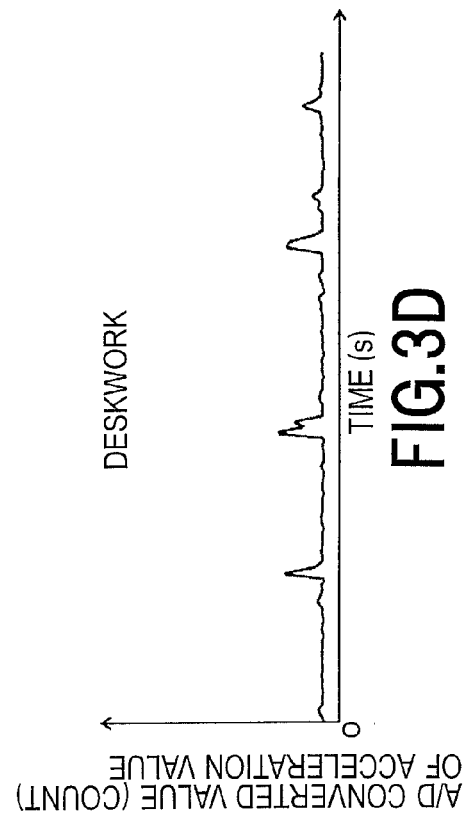
FIG. 3B is a drawing showing a waveform of the A/D converted value of the acceleration value as second registered body movement data in the same example.
Figure 3C:
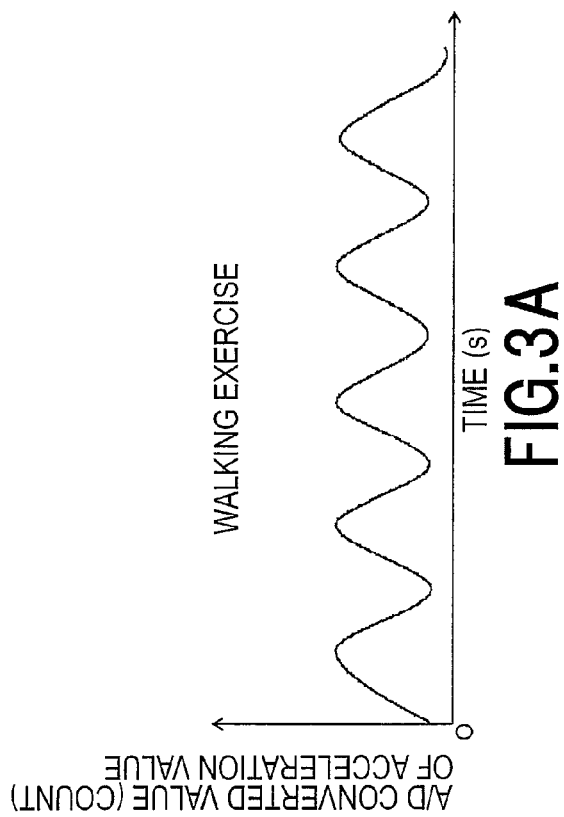
FIG. 3C is a drawing showing a waveform of the A/D converted value of the acceleration value as third registered body movement data in the same example.
Figure 3D:
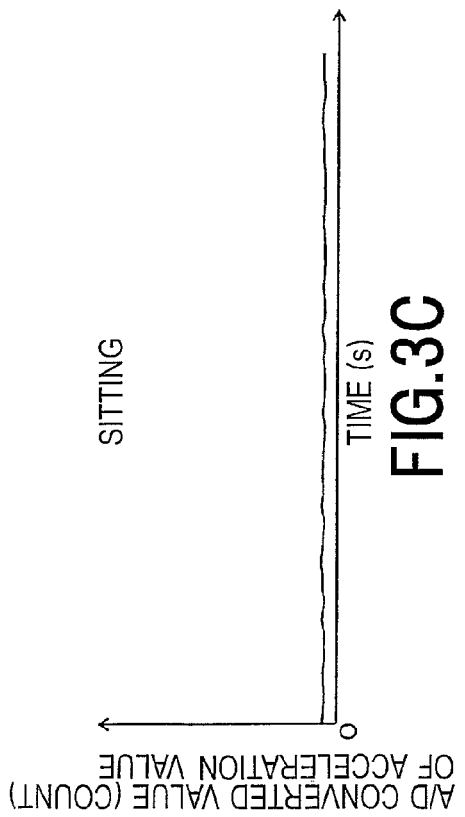
FIG. 3D is a drawing showing a waveform of the A/D converted value of the acceleration value as fourth registered body movement data in the same example.
Figure 4A:
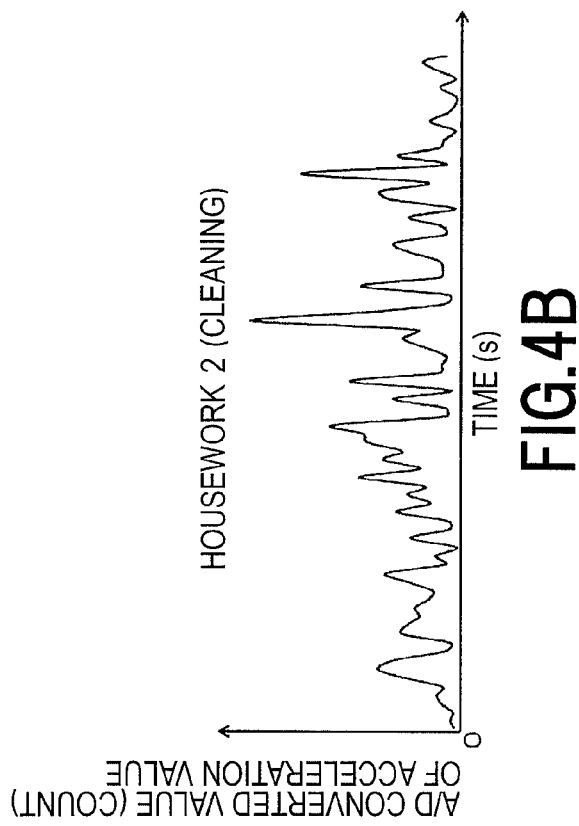
FIG. 4A is a drawing showing a waveform of the A/D converted value of the acceleration value as fifth registered body movement data in the example of the registered body movement data to be registered in the initial setting of the body movement detecting apparatus.
Figure 4B:
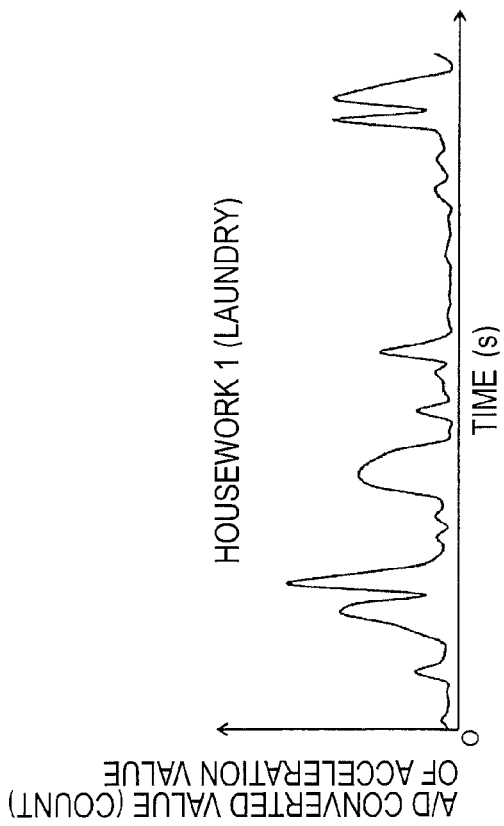
FIG. 4B is a drawing showing a waveform of the A/D converted value of the acceleration value as sixth registered body movement data in the same example.
Figure 4C:
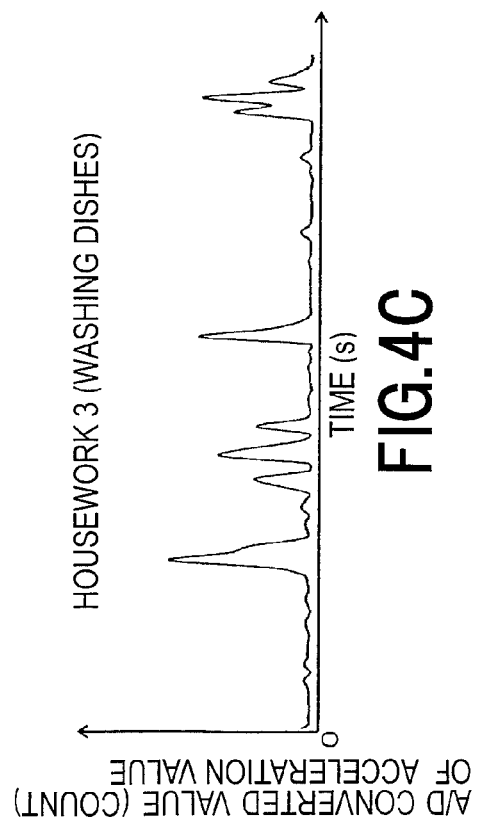
FIG. 4C is a drawing showing a waveform of the A/D converted value of the acceleration value as seventh registered body movement data in the same example.

First of all, referring now to FIG. 2 to FIG. 4, the initial setting (registered body movement data acquiring step) of the body movement detecting apparatus 10 will be described. FIG. 2 is a flowchart showing an example of a flow of the initial setting of the body movement detecting apparatus according to the invention; FIG. 3A is a drawing showing a waveform of the A/D converted value of the acceleration value as the first registered body movement data in an example of the registered body movement data to be registered in the initial setting of the body movement detecting apparatus according to the invention; FIG. 3B is a drawing showing a waveform of the A/D converted value of the acceleration value as the second registered body movement data in the same example; FIG. 3C is a drawing showing a waveform of the A/D converted value of the acceleration value as the third registered body movement data in the same example; FIG. 3D is a drawing showing a waveform of the A/D converted value of the acceleration value as the fourth registered body movement data in the same example; FIG. 4A is a drawing showing a waveform of an A/D converted value of the acceleration value as the fifth registered body movement data in the same example; FIG. 4B is a drawing showing a waveform of the A/D converted value of the acceleration value as the sixth registered body movement data in the same example; FIG. 4C is a drawing showing a waveform of the A/D converted value of the acceleration value as the seventh registered body movement data in the same example.

After having activated the body movement detecting apparatus 10, the user operates the operating unit 21, inputs the biological data required mainly for calculating the consumed energy (for example, weight, age, sex, etc.), and causes the input biological data to be memorized in a predetermined area of the memory 33 (Step S1).

Subsequently, the controller 40 displays the guidance for guiding the setting of the registered body movement data on the display unit 22 (Step S2). As the display of the guidance, it is preferable to list up the plurality of types of the activities of the registered body movement data, which can be registered, such as the first registered body movement data "walking", the second registered body movement data "running", the third registered body movement data "watching TV or listening to the music in the quietly sitting position", the fourth registered body movement data "light work in the office", the fifth registered body movement data "housework 1 (laundry)", the sixth registered body movement data "housework 2 (cleaning)", the seventh registered body movement data "housework 3 (washing dishes)" so as to allow the user to select items.

The controller 40 causes the user to operate the operating unit 21 and select a type of the activity of the registered body movement data which the user wants to register, and goes standby so as to memorize the selected items in the memory 33 in correspondence with the body movement data which are acquired immediately after (Step S3). Subsequently, the controller 40 causes the display unit 22 to display a window which prompts the user to perform the activity corresponding to the selected type of the activity of the registered body movement data (for example, "walking"), and acquires the body movement data from the activity ("walking") of the user in a state in which the body movement detecting apparatus 10 is attached to a predetermined position on a dressing or the like of the user (Step S4). Whether or not the predetermined unit time (for example, 20 seconds) has elapsed from the start of the acquisition of the body movement data is counted by the timer 34 and, if not (No in Step S5), the acquisition of the body movement data is continued without change (Step S4).

When the predetermined unit time is elapsed from the start of the acquisition of the body movement data (Yes in Step S5), the controller 40 calculates the determination value of the acquired body movement data (Step S6). The determination value is calculated as follows, for example. The controller 40 causes the A/D converter 35 to convert the acceleration values acquired by the accelerator sensor 31 according to the body movement of the user from analogue to digital and causes the memory 33 to memorize the acquired digital acceleration values in sequence in time series, and acquires a waveform by plotting all the A/D converted values of the acceleration values acquired in sequence with a lateral axis indicating the elapsed time (unit: second) and a vertical axis indicating the A/D converted value of the acceleration value (unit: count) (see FIG. 3 and FIG. 4). The acquired waveform is subjected to the frequency analysis, then characteristic or representative (two, for example) frequency zones are selected, and peak-to-peak values (P-P value), average values, maximum values, and minimum values in these frequency zones are calculated respectively, and at least one of these values is employed as the determination value.

The A/D converted value of the acceleration value, the waveform thereof, and the predetermined determination value as the body movement data acquired in this manner are memorized in the memory 33 as the registered body movement data selected in Step S3 (first registered body movement data) (Step S7) and the corresponding body activity strength is also memorized together. The corresponding body activity strength means the body activity strength preset for each type of the activity displayed in the guidance in Step S2. For example, the body activity strength corresponding to each of the body movement data is set such as a body activity strength "3.0" for the body movement data "walking", a body activity strength "7.0" for the body movement data "running", a body activity strength "1.0" for the body movement data "watching TV or listening to the music in the quietly sitting position", a body activity strength "1.5" for the body movement data "light work in the office", a body activity strength "2.0" for the body movement data "housework 1 (laundry)", a body activity strength "2.5" for the body movement data "housework 2 (cleaning)", and a body activity strength "2.3" for the body movement data "housework 3 (washing dishes)".

Subsequently, the controller 40 displays the guidance asking whether the setting for other registered body movement data continuously is wanted on the display unit 22 (Step S8). When the user operates the operating unit 21 and selects to continue (Yes in Step S8), the procedure goes back to Step S2 and the process is repeated. If the user selects to end (No in Step S8), the initial setting of the body movement detecting apparatus 10 is ended.

For example, when the user performs an initial registration of "walking" as the registered body movement data, the user selects the first registered body movement data "walking" in the guidance in Step S2. Subsequently, the user performs the "walking" for the predetermined unit time and inputs the body movement data of the "walking" as the individual user into the body movement detecting apparatus 10 in Step S3. The body movement detecting apparatus 10 acquires and calculates the A/D converted value of the acceleration value, the waveform thereof (see FIG. 3A), and the predetermined determination value, memorizes these values as the first registered body movement data of the "walking" of the corresponding individual user, and indexes the body activity strength "3.0". The same can be said for other body movement data such as "running" (FIG. 3B), "watching TV or listening to the music in the quietly sitting position" (FIG. 3C), "light work in the office" (FIG. 3D), "housework 1 (laundry)" (FIG. 4A), "housework 2 (cleaning)" (FIG. 4B), and "housework 3 (washing dishes)" (FIG. 4C).

Figure 5:
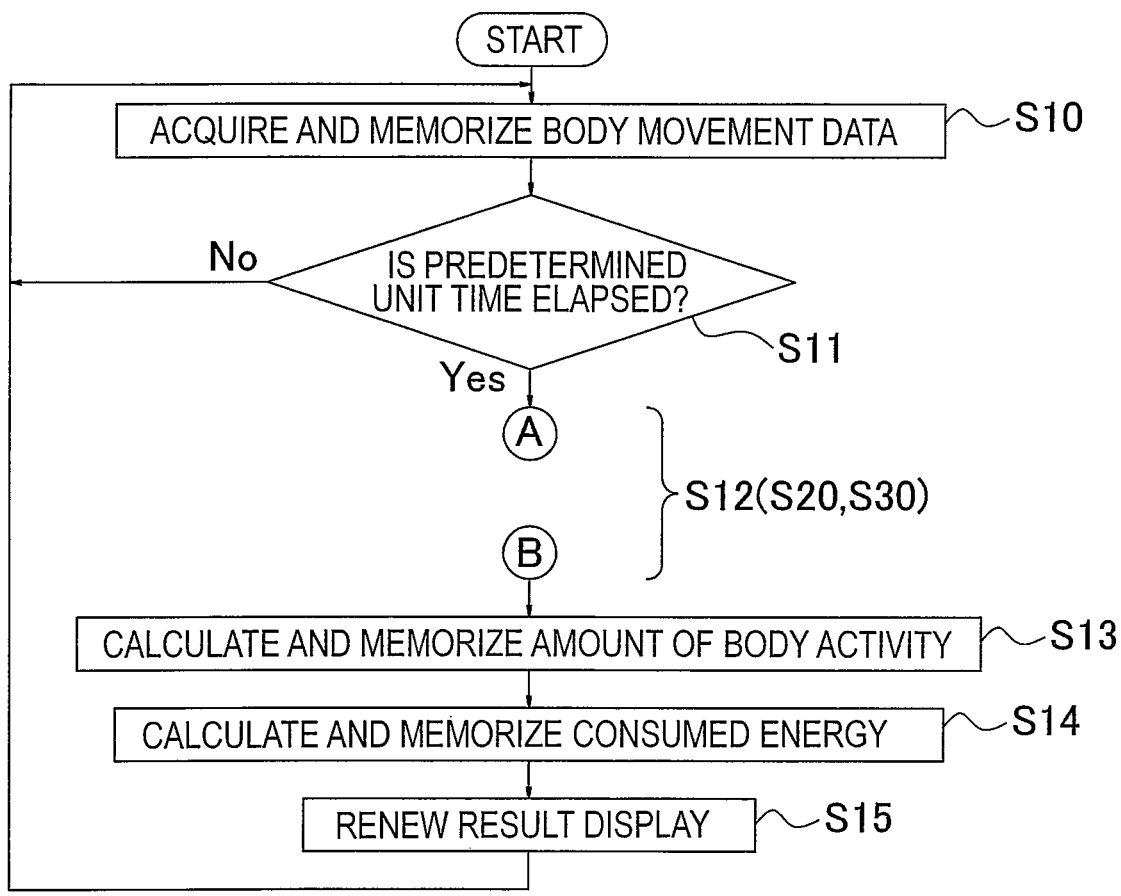
FIG. 5 is a flowchart showing an example of a flow of an operation of the body movement detecting apparatus according to the invention.
Figure 6:
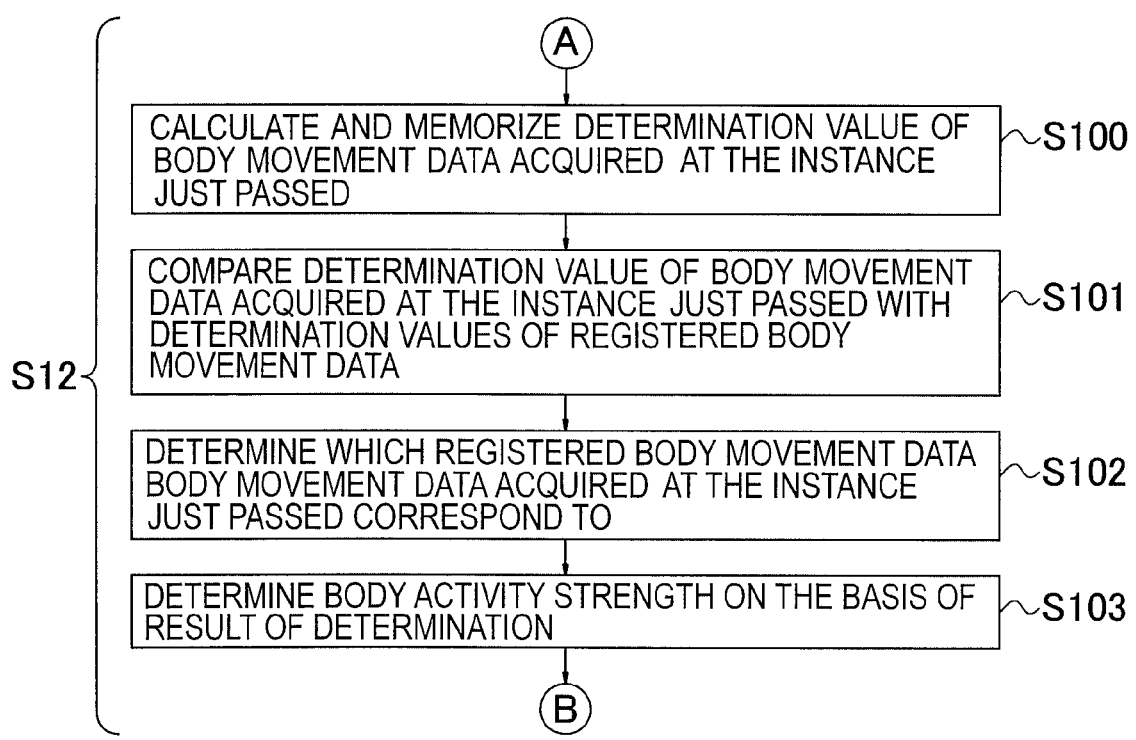
FIG. 6 is a flowchart showing a body movement determining process of the body movement detecting apparatus according to the invention.

Referring now to FIG. 5 to FIG. 6, a flow of calculation of the consumed energy by the body movement detecting apparatus 10 will be described. Here, FIG. 5 is a flowchart showing an example of a flow of an operation of the body movement detecting apparatus according to the invention, and FIG. 6 is a flowchart showing a body movement determining process of the body movement detecting apparatus according to the invention.

After having ended the above-described initial setting, the body movement detecting apparatus 10 is attached to the predetermined position on the dressing or the like of the user. When the utilization of the body movement detecting apparatus 10 is started, the body movement data of the user are acquired by the body movement detecting apparatus 10, and are memorized in the memory 33 (Step S10) (body movement data acquiring step). More specifically, the acceleration values of the body movement of the user are acquired by the accelerator sensor 31, then, the A/D converter 35 converts the respective output values acquired by the X-axis sensor 31a, the Y-axis sensor 31b, and the Z-axis sensor 31c of the accelerator sensor 31 as analogue data into digital data, and the controller 40 simultaneously acquires the elapsed time (or the current time of day) from the time point when the acquisition is started by the timer 34, and causes the memory 33 to memorize the A/D converted values of the respective output values in correspondence with the predetermined elapsed time (or the current time of day) from the start of the acquisition. Whether or not the predetermined unit time (for example, 20 seconds) has elapsed from the start of the acquisition of the body movement data is counted by the timer 34 and, if not (No in Step S11), the acquisition and the memory of the body movement data are continued without change (Step S10).

When the predetermined unit time is elapsed from the start of the acquisition of the body movement data (Yes in Step S11), a body movement determining process for determining which the registered body movement data the body movement data acquired at the instance just passed correspond to is performed (Step S12) (body movement determining step). The body movement determining process is for comparing determination values of the body movement data acquired individually per the predetermined unit time with the determination values of the registered body movement data which are already registered after the initial setting, and determining which registered body movement data they correspond to, which will be described with reference to FIG. 6. As Steps from A to B in FIG. 5, Steps from A to B in Step S12 in FIG. 6 are executed.

The controller 40 calculates the determination value of the body movement data acquired at the instance just passed and causes the memory 33 to memorize the same (Step S100). The determination value may be calculated in the same manner as the determination value of the registered body movement data. The controller 40 causes the A/D converter 35 to convert the acceleration values acquired by the accelerator sensor 31 according to the body movement of the user from analogue to digital and causes the memory 33 to memorize the acquired digital acceleration values in sequence in time series, and acquires the waveform by plotting all the A/D converted values of the acceleration values acquired in sequence with the lateral axis indicating the elapsed time (unit: second) and the vertical axis indicating the A/D converted value of the acceleration value (unit: count) . The acquired waveform is subjected to the frequency analysis, then the characteristic or representative (two, for example) frequency zones are selected, and the P-P value, the average value, the maximum value, and the minimum value in these frequency zones are calculated respectively, and at least one of these values is employed as the determination value.

Subsequently, the controller 40 compares the determination value of the body movement data acquired at the instance just passed with the determination values of the registered body movement data which are already registered (Step S101). This comparing process is performed on all the registered body movement data which are already registered in sequence. Consequently, the controller 40 selects the determination value of the body movement data acquired at the instance just passed which corresponds to the determination value of the registered body movement data, and determines which the type of the activity of the registered body movement data the body movement data acquired at the instance just passed correspond to (Step S102). In the determination of whether or not the body movement data acquired at the instance just passed corresponds to the determination values of the registered body movement data, an arbitrary predetermined range is determined, and those having difference of the determination values from the determination value of the registered body movement data falling within the predetermined range are determined to match as well as those which match completely.

The body activity strength of the body movement data acquired at the instance just passed is determined on the basis of the result of determination (Step S103). More specifically, in the case of the result of determination such that the body movement data acquired at the instance just passed correspond to the first registered body movement data "walking" (FIG. 3A) from the registered body movement data, the body activity strength of the body movement data acquired at the instance just passed is determined as "3.0" on the basis of the body activity strength "3.0" indexed to the type of the activity of the determined first registered body movement data.

After having performed the body movement determining process (Step S12) as described above, the controller 40 causes the computer 32 to calculate the amount of the body activity on the basis of the body movement data acquired at the instance just passed in the predetermined unit time, and causes the memory 33 to memorize the same (Step S13) as shown in FIG. 5. The amount of the body activity is calculated by multiplying a body activity strength determined in Step S103 by the predetermined unit time (20 seconds in this embodiment).

Furthermore, the controller 40 causes the computer 32 to calculate the consumed energy on the basis of the body movement data acquired at the instance just passed in the predetermined unit time, and causes the memory 33 to memorize the calculated consumed energy (Step S14) (energy computing step). The consumed energy in the predetermined unit time is calculated by multiplying the amount of the body activity obtained in Step S13 by the weight of the user which is registered in advance and the predetermined coefficient.

The consumed energy in predetermined unit time calculated in this manner is accumulated per the predetermined unit time, and the total value is renewed as a result display on the display unit 22 (Step S15). In other words, the consumed energy in the first predetermined unit time calculated as described above is displayed as the result display on the display unit 22 as is, then the procedure goes back to Step S10. Then, the consumed energy in the second predetermined unit time is calculated, then the consumed energy in the first predetermined unit time and the consumed energy in the second predetermined unit time are added, and the display on the display unit 22 is renewed with an added total value as the result display. The consumed energy in the third predetermined unit time is also calculated, and the result display is renewed. The result display is not limited to the consumed energy, but may include the total number of steps which are counted by the controller 40.

(First Modification)

Figure 7:
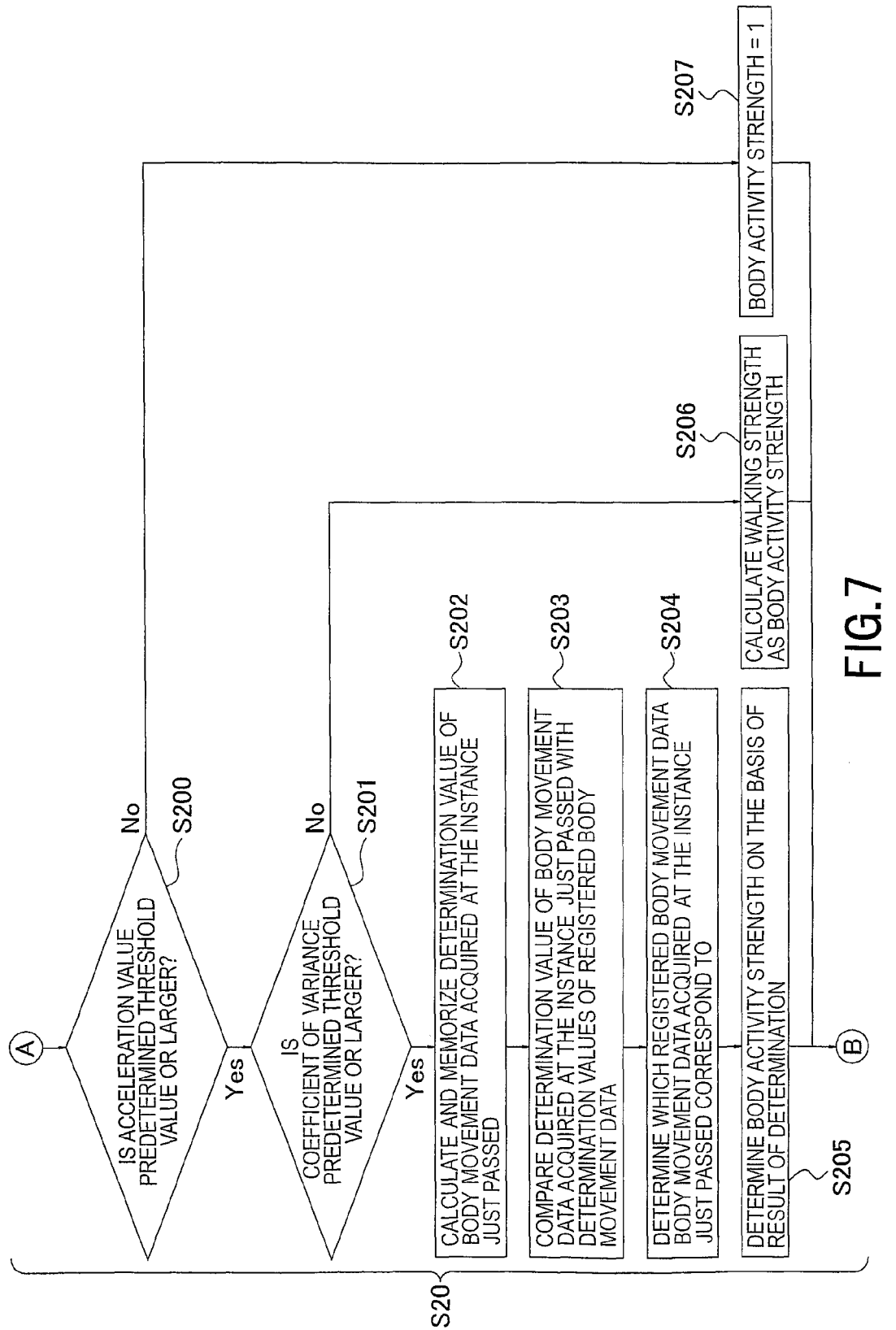
FIG. 7 is a flowchart showing a body movement determining process of the body movement detecting apparatus according to a first modification of the invention.

The body movement detecting apparatus and the body movement detecting method according to the invention are capable of performing a body movement determining process according to first modification shown in Step S20 in FIG. 7 instead of the body movement determining process shown in Step S12 in FIGS. 5 and 6. In other words, in the first modification, as the Steps from A to B in FIG. 5, Steps from A to B in Step S20 in FIG. 7 are executed. FIG. 7 is a flowchart showing the body movement determining process of the body movement detecting apparatus according to the first modification of the invention.

In the first modification shown in FIG. 7, as regards the predetermined activity of the user, even though the registered body movement data are not registered in advance, it is determined that the user is performing the predetermined activity, so that the calculation of the consumed energy is enabled. Accordingly, the labor of registration of the registered body movement data may be alleviated, and the user friendliness is improved. More specifically, as shown in FIG. 7, the body movement determining process according to the first modification in which the operation to be done by the user for registering the registered body movement data in the resting state and the registered body movement data relating to the type of the activity of the walking may be omitted by enabling the determination of whether the user is in the resting state, walking (including running), or performing other activities according to an acceleration value and a coefficient of variance will be described.

First of all, the controller 40 determines whether or not the acceleration value of the body movement data acquired at the instance just passed in the predetermined unit time in Step S11 in FIG. 5 is a predetermined threshold value or larger (Step S200). The predetermined threshold value is a threshold value relating to the acceleration value which determines that the user is in activity when the acceleration value is the threshold value or larger, and an arbitrary value is set as a default value. When the acceleration value of the body movement data acquired at the instance just passed does not reach the predetermined threshold value (No in Step S200), the controller 40 determines that the user is not moving (or in the resting state, or sleeping), and causes the memory 33 to memorize this state as the body activity strength "1" (Step S207).

On the other hand, when the acceleration value of the body movement data acquired at the instance just passed is the predetermined threshold value or larger (Yes in Step S200), the controller 40 determines whether or not the coefficient of variance of the body movement data acquired at the instance just passed is the predetermined threshold value or larger (Step S201). More specifically, when observing the transition of the acceleration value while the user is walking in the predetermined unit time in Step S11 in FIG. 5, amplitude at pitches corresponding to the respective steps is confirmed. Therefore, it is determined that the user is walking when the steps having a predetermined amplitude at a predetermined pitch, for example, are confirmed in the body movement data acquired at the instance just passed within a predetermined time, that is, when they are stable and regular without variations such that the coefficient of variance does not exceed the predetermined threshold value, so that the number of steps is counted. The coefficient of variance is a value obtained by dividing a standard deviation by an average value.

When the coefficient of variance of the body movement data acquired at the instance just passed does not reach the predetermined threshold value (No in Step S201), the controller 40 determines that the user is walking, and causes the computer 32 to calculate a walking strength as the body activity strength, and causes the memory 33 to memorize the result of calculation (Step S206). The walking strength may be calculated on the basis of the magnitude of the acceleration value.

On the other hand, when the coefficient of variance of the body movement data acquired at the instance just passed is the predetermined threshold value or larger (Yes in Step S201), the controller 40 calculates the determination value of the body movement data acquired at the instance just passed and causes the memory 33 to memorize the same (Step S202). As the determination value, it may be calculated in the same manner as the embodiment shown in FIG. 6. The controller 40 causes the A/D converter 35 to convert the acceleration values acquired by the accelerator sensor 31 according to the body movement of the user from analogue to digital and causes the memory 33 to memorize the acquired digital acceleration values in sequence in time series, and acquires a waveform by plotting all the A/D converted values of the acceleration values acquired in sequence with the lateral axis indicating the elapsed time (unit: second) and the vertical axis indicating the A/D converted value of the acceleration value (unit: count). The acquired waveform is subjected to the frequency analysis, then the characteristic or representative (two, for example) frequency zones are selected, and the peak-to-peak value (P-P value), the average value, the maximum value, and the minimum value in these frequency zones are calculated respectively, and at least one of these values is employed as the determination value.

Subsequently, the controller 40 compares the determination value of the body movement data acquired at the instance just passed with the determination values of the registered body movement data which are already registered (Step S203). This comparing process is performed on all the registered body movement data which are already registered in sequence. Consequently, the controller 40 selects the determination value of the body movement data acquired at the instance just passed which corresponds to the determination value of the registered body movement data, and determines which the type of the activity of the registered body movement data the body movement data acquired at the instance just passed correspond to (Step S204).

Then, the body activity strength of the body movement data acquired at the instance just passed is determined on the basis of the result of determination (Step S205). More specifically, in the case of the result of determination such that the body movement data acquired at the instance just passed correspond to the first registered body movement data "walking" (FIG. 3A) from the registered body movement data, the body activity strength of the body movement data acquired at the instance just passed is determined as "3.0" on the basis of the body activity strength "3.0" indexed to the type of the activity of the determined first registered body movement data.

After having performed the body movement determining process (step S20) as described above, the controller 40 causes the computer 32 to calculate the amount of the body activity on the basis of the body movement data acquired at the instance just passed in the predetermined unit time, and causes the memory 33 to memorize the same (Step S13) as shown in FIG. 5. The amount of the body activity is calculated by multiplying the body activity strength acquired in Step S205, Step S206, or Step S207 by the predetermined unit time (20 seconds in this embodiment).

Furthermore, the controller 40 causes the computer 32 to calculate the consumed energy on the basis of the body movement data acquired at the instance just passed in the predetermined unit time, and causes the memory 33 to memorize the calculated consumed energy (Step S14) (energy computing step). The consumed energy in predetermined unit time is accumulated per the predetermined unit time, and the total value is renewed as the result display on the display unit 22 (Step S15).

According to the first modification as described above, whether the user is in the resting state or walking (or running) can be determined automatically, it is not necessary to register the registered body movement data relating to these types of the activity specifically, and hence the registration operation to be done by the user can be omitted.

(Second Modification)

Figure 8:
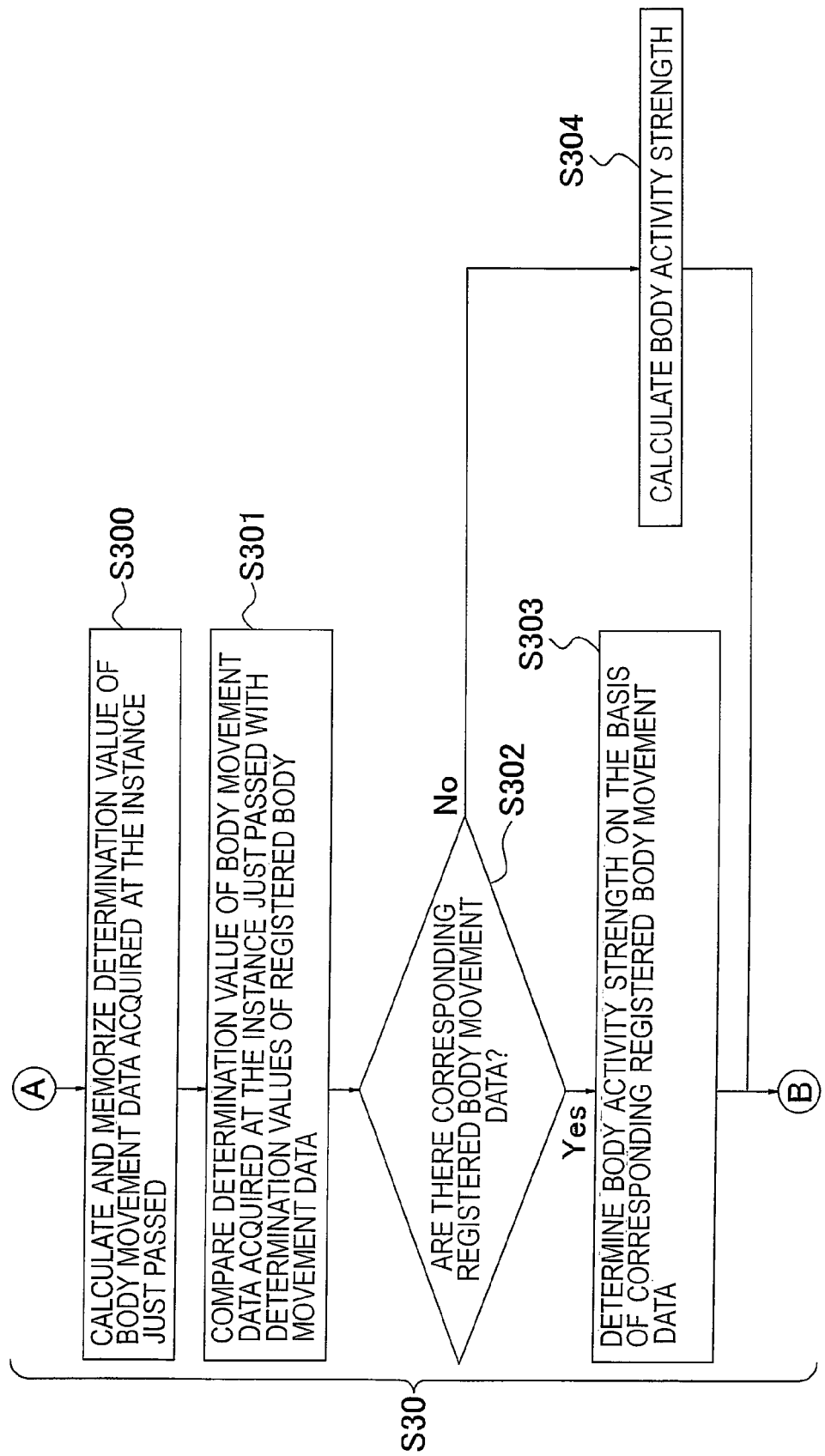
FIG. 8 is a flowchart showing a body movement determining process of the body movement detecting apparatus according to a second modification of the invention.

Subsequently, referring now to FIG. 8, a second modification of the invention will be described. FIG. 8 is a flowchart showing a body movement data determining process of the body movement detecting apparatus according to the second modification of the invention. In the second modification, the body movement determining process shown in Step S30 in FIG. 8 is performed instead of the body movement determining process shown in Step S12 in FIGS. 5 and 6. In other words, in the second modification, as the Steps from A to B in FIG. 5, Steps from A to B in Step S30 in FIG. 8 are executed.

In the second modification shown in FIG. 8, the different methods of calculation of the body activity strength are provided for the case where the determination value corresponding to the determination values of the registered body movement data relating any type of activity is found and the case where it is not found as a result of comparing the determination value of the body movement data acquired at the instance just passed with the determination values of the registered body movement data.

First of all, the controller 40 calculates the determination value of the body movement data acquired at the instance just passed in the predetermined unit time in Step S11 in FIG. 5 and causes the memory 33 to memorize the same (Step S300). As the determination value, it may be calculated in the same manner as the example shown in FIG. 6 or FIG. 7.

Subsequently, the controller 40 compares the determination value of the body movement data acquired at the instance just passed with the determination values of the registered body movement data which are already registered (Step S301). This comparing process is performed on all the registered body movement data which are already registered in sequence. As a result of the comparing process, the controller 40 determines whether or not there is any body movement data acquired at the instance just passed corresponding to the determination value of the registered body movement data (Step S302).

As the result of the comparing process as regards the determination value of the body movement data acquired at the instance just passed, if there is registered body movement data corresponding to the determination value of the body movement data acquired at the instance just passed (Yes in Step S302), the body activity strength of the body movement data acquired at the instance just passed is determined on the basis of the types of the activity of the registered body movement data.

In contrast, as the result of the comparing process as regards the determination value of the body movement data acquired at the instance just passed, if there is no registered body movement data corresponding to the determination value of the body movement data acquired at the instance just passed (No in Step S302), the controller 40 causes the computer 32 to calculate the body activity strength on the basis of the body movement data acquired at the instance just passed in the predetermined unit time and causes the memory 33 to memorize the result of calculation (Step S304). The body activity strength may be calculated, for example, on the basis of the magnitude of the acceleration value.

After having performed the body movement determination process (Step S30) as described above, the controller 40 causes the computer 32 to calculate the amount of the body activity on the basis of the body movement data acquired at the instance just passed in the predetermined unit time, and causes the memory 33 to memorize the same (Step S13) as shown in FIG. 5. The amount of the body activity is calculated by multiplying the body activity strength acquired in Step S303, or Step S304 by the predetermined unit time (20 seconds in this embodiment).

Furthermore, the controller 40 causes the computer 32 to calculate the consumed energy on the basis of the body movement data acquired at the instance just passed in the predetermined unit time, and causes the memory 33 to memorize the calculated consumed energy (Step S14) (energy computing step). The consumed energy in the predetermined unit time is accumulated per the predetermined unit time, and the total value is renewed as the result display on the display unit 22 (Step S15).

According to the body movement detecting apparatus and the body movement detecting method described in the embodiment and in the first and second modifications described above, the type of the activity can be determined using the registered body movement data of the individual user, and the consumed energy can be calculated using the body activity strength determined or calculated according to the type of the activity. Therefore, the consumed energy for the body movement generated by the activity of the user can be calculated in view of the characteristics thereof.

Although the invention has been described on the basis of the above-described embodiment, the invention is not limited to the above-described embodiment, and may be improved or modified within the scope of the object of the improvement and the sprit of the invention.

INDUSTRIAL APPLICABILITY

As described thus far, the body movement detecting apparatus and the body movement detecting method according to the invention are effected when the consumed energy of the body movement generated by the activity of the user needs to be grasped in view of its characteristic.

What is claimed is:
1. A body movement detecting apparatus comprising:
a body movement data acquiring sensor configured to detect a body movement of a user and acquire body movement data relating to the body movement of the user and including an acceleration value relating to the body movement of the user;
a memory coupled with the body movement data acquiring sensor;
a controller configured to:
(i) determine, if registered body movement data is memorized in the memory, which has been acquired in advance using the body movement data acquiring sensor, whether any of the registered body movement data memorized in the memory corresponds in type to a just passed activity of user; and
(ii) upon determining that one of the registered body movement data memorized in the memory corresponds in type to the just passed activity of user in (i), determine a type of the just passed activity by comparing body movement data of the just passed activity with the one of the registered body movement data; and a computer configured to:
if the type of the just passed activity is determined in (ii), calculate consumed energy resulting from the body movement based on the determined type of the just passed activity determined by the controller; and
if the controller determines that no body movement data are registered in the memory or none of the registered body movement data corresponds in type to the just passed activity in (i), calculate the consumed energy resulting from the body movement of the just passed activity based on at least an acceleration value in the body movement data of the just passed activity, without comparing the body movement data of the just passed activity with the registered body movement data.

2. The body movement detecting apparatus according to claim 1, wherein the computer is further configured to calculate the consumed energy using a body activity strength corresponding to the determined type of the just passed activity determined by the controller.

3. The body movement detecting apparatus according to claim 2, wherein
the computer is configured to calculate the consumed energy based on the body activity strength corresponding to the determined type of the just passed activity, when the controller determines that the one of the registered body movement data are memorized in the memory in (i), and to calculate the consumed energy on the basis of a body activity strength calculated based on a body movement strength of the body movement data, when the controller determines that no body movement data are registered in the memory or none of the registered body movement data corresponds in type to the just passed activity in (i).

4. The body movement detecting apparatus according to claim 2, wherein:
the controller is further configured, if the controller determines that no body movement data are registered in the memory or none of the registered body movement data corresponds in type to the just passed activity in (i), to determine the type of the just passed activity by comparing the acceleration value with a threshold value.

5. The body movement detecting apparatus according to claim 4, wherein, if the controller determines that no body movement data are registered in the memory or none of the registered body movement data corresponds in type to the just passed activity in (i):
the controller is configured to determine, without using the registered body movement data, whether or not the user is in a moving state or in a non-moving state by using a threshold value,
if the controller determines that the user is in the non-moving state, the computer is configured to calculate the consumed energy based on a body activity strength in the resting state, and
if the controller determines that the user is in the moving state, the computer is configured to calculate the consumed energy based on at least the acceleration value in the body movement data of the just passed activity.

6. The body movement detecting apparatus according to claim 4, wherein the controller is configured to determine, if the controller determines that no body movement data are registered in the memory or none of the registered body movement data corresponds in type to the just passed activity in (i), that the user is not moving, is in a resting state or is sleeping if the acceleration value does not exceed the threshold value.

7. The body movement detecting apparatus according to claim 6, wherein the controller is configured to determine, if the controller determines that no body movement data are registered in the memory or none of the registered body movement data corresponds in type to the just passed activity in (i), that the user is walking if the acceleration value exceeds the threshold value and a variance of the acceleration value does not exceed a predetermined value.

8. The body movement detecting apparatus according to claim 1, further comprising an input device configured to input a first type of activity,
wherein the memory is configured to memorize the registered body movement data in correspondence with the first type of activity input by the input device.

9. The body movement detecting apparatus according to claim 8, wherein:
the memory is configured to memorize one or more types of activities together with body activity strengths for the respective one or more types of the activities, and
the input device is configured to allow the user to select a desired type of activity from the one or more types of the activities memorized in the memory, and to cause the registered body movement data to be memorized in the memory in correspondence with the selected type of activity.

10. The body movement detecting apparatus according to claim 1, wherein the type of the just passed activity determined by the computer is walking or running.

11. The body movement detecting apparatus according to claim 1, wherein the registered body movement data are acquired by the body movement data acquiring sensor and memorized in the memory.

12. The body movement detecting apparatus according to claim 1, wherein the controller and the computer are integrated into an integrated circuit.

13. A body movement detecting method comprising:
a body movement acquiring step of detecting, by using a sensor, a body movement of a user and acquiring body movement data relating to the body movement of the user and including an acceleration value relating to the body movement of the user;
a body movement determining step of:
(i) determining, by a controller, if registered body movement data is memorized in the memory, which has been acquired in advance using the body movement data acquiring sensor, whether any of the registered body movement data memorized in the memory corresponds in type to a just passed activity of user; and
(ii) upon determining that one of the registered body movement data memorized in the memory corresponds in type to the just passed activity of user in (i), determining, by the controller, a type of the just passed activity by comparing body movement data of the just passed activity with the one of the registered body movement data; and
an energy computing step of:
if the type of the just passed activity is determined in (ii), calculating, by a computer, consumed energy resulting from the body movement based on the determined type of the just passed activity; and
if it is determined that that no body movement data are registered in the memory or none of the registered body movement data corresponds in type to the just passed activity in (i), calculating, by the computer, the consumed energy resulting from the body movement of the just passed activity based on at least an acceleration value in the body movement data of the just passed activity, without comparing the body movement data of the just passed activity with the registered body movement data.

14. The body movement detecting method according to claim 13, wherein:
if it is determined that that no body movement data are registered in the memory or none of the registered body movement data corresponds in type to the just passed activity in (i), the type of the just passed activity is determined by comparing the acceleration value with a threshold value.

15. The body movement detecting method according to claim 14, wherein, if it is determined that that no body movement data are registered in the memory or none of the registered body movement data corresponds in type to the just passed activity in (i), it is determined in the body movement determining step that the user is not moving, is in a resting state or is sleeping if the acceleration value does not exceed the threshold value.

16. The body movement detecting method according to claim 15, wherein, if it is determined that that no body movement data are registered in the memory or none of the registered body movement data corresponds in type to the just passed activity in (i), it is determined in the body movement determining step that the user is walking if the acceleration value exceeds the threshold value and a variance of the acceleration value does not exceed a predetermined value.

17. The body movement detecting method according to claim 13, further comprising a registered body movement data acquiring step of acquiring, by the sensor, the registered body movement data and storing the registered body movement data in relation with a type of activity in the memory.

18. The body movement detecting method according to claim 13, wherein the controller and the computer are integrated into an integrated circuit.

* * * * *